United States Patent [19]

Messier et al.

[11] Patent Number: 4,624,256
[45] Date of Patent: Nov. 25, 1986

[54] CAPROLACTONE POLYMERS FOR SUTURE COATING

[75] Inventors: Kenneth A. Messier, Jewett City; Joseph D. Rhum, Old Lyme, both of Conn.

[73] Assignee: Pfizer Hospital Products Group, Inc., New York, N.Y.

[21] Appl. No.: 774,636

[22] Filed: Sep. 11, 1985

[51] Int. Cl.[4] ............................................. A61L 17/00
[52] U.S. Cl. ................................................. 128/335.5
[58] Field of Search ..................................... 132/335.5

[56] References Cited

U.S. PATENT DOCUMENTS

| | | | |
|---|---|---|---|
| 3,773,737 | 11/1973 | Goodman | 128/335.5 |
| 3,867,190 | 2/1975 | Schmitt | 128/335.5 |
| 3,896,814 | 7/1975 | Vivien | 128/335.5 |
| 3,918,455 | 11/1975 | Coplan | 128/335.5 |
| 3,942,532 | 3/1976 | Hunter | 128/335.5 |
| 4,201,216 | 5/1980 | Mattei | 128/335.5 |

OTHER PUBLICATIONS

Sagarin, Cosmetics Science & Technology, 1957, pp. 104–105.

Primary Examiner—Gregory E. McNeill
Attorney, Agent, or Firm—Charles J. Knuth; Peter C. Richardson; Gezina Holtrust

[57] ABSTRACT

High molecular weight caprolactone polymers are coated on surgical sutures to improve suture properties such as smooth surface, single knot slipdown, two throw knot slipdown for repositioning, and three throw knot security.

8 Claims, No Drawings

CAPROLACTONE POLYMERS FOR SUTURE COATING

BACKGROUND OF THE INVENTION

The invention relates to surgical sutures comprising a braided multifilament of a biocompatible material coated with a lubricating agent. More particularly, the invention relates to sutures coated with high molecular weight polycaprolactone or a high molecular weight copolymer of at least 90% by weight of caprolactone.

Coating of braided sutures with lubricating agents to improve knot slipdown properties is known in the art. For instance, U.S. Pat. No. 4,080,969 discloses coating braided polyglycolic acid filaments with diglycolate polyesters. U.S. Pat. No. 4,027,676 provides a coating for sutures comprising a bioabsorbable film-forming polymer, the bioabsorbable lubricant polyalkylene glycol and a hydrophobic material. U.S. Pat. No. 3,867,190 relates to polyglycolic acid sutures coated with a copolymer of lactic and glycolic acid. This patent also mentions incorporation of caprolactone in glycolide sutures. The formed copolymer contains not more than 15% by weight of caprolactone. Use of such copolymer in coating of sutures is not suggested.

U.S. Pat. No. 3,942,532 describes polyester multifilament sutures coated with polycaprolactone Niax Polyol D-560 having a low molecular weight of about 2,000 and a melt viscosity at 60° C. of 500 centipoise.

It is an object of the invention to provide a suture having a smooth surface, good single knot slipdown, two throw knot slipdown for repositioning, and three throw knot security.

SUMMARY OF THE INVENTION

In accordance with the invention, there is provided a surgical suture of a braided multifilament biocompatible, bioabsorbable material coated with a lubricating agent selected from the group consisting of high molecular weight polycaprolactone, a high molecular weight copolymer derived from at least 90% by weight of caprolactone and the remainder another biodegradable monomer, and a blend of at least 50% by weight of said polycaprolactone or said copolymer and up to 50% by weight of another biodegradable lubricating agent, based on the combined weights of the lubricating agents. The homopolymer or copolymer of caprolactone has a melt viscosity at 60° C. of at least about 50,000 centipoise (cps) or is a solid.

Generally, the lubricating agent or agents are present in an amount of about 0.5 to 10% by weight based on the suture.

The invention also provides for a needled surgical suture wherein a novel coated suture as described above is threaded through or fitted with a surgical needle, and a surgical suture package comprising a sterile enclosure containing a sterile needled coated surgical suture as previously described.

DETAILED DESCRIPTION OF THE INVENTION

According to the invention, any conventional bioabsorbable suture material may be used. Sutures must be biocompatible such that they do not cause any adverse reactions in living tissue. The sutures of the invention are bioabsorbable such that they are slowly absorbed in living tissue. Examples of suitable bioabsorbable suture materials are collagen, poly(glycolic acid), poly(lactic acid), poly(hydroxybutyric acid), chitosan, chitin, carboxymethylcellulose etc. Preferably, the suture is made of poly(glycolic acid) or a glycolic acid copolymer containing at least 85% glycolic acid units.

The primary lubricating agent of the invention is high molecular weight polycaprolactone or a high molecular weight copolymer of at least 90% by weight of caprolactone and at most 10% by weight of another biodegradable monomer. Examples of such biodegradable monomers are glycolic acid, a glycolide, lactic acid, a lactide, p-dioxanone, valerolactone and other lactones derived from linear aliphatic hydroxycarboxylic acids, α-hydroxybutyric acid, ethylene carbonate, ethylene oxide, propylene oxide, propylene carbonate, malic acid ester lactones, succinic acid, adipic acid and other linear aliphatic dicarboxylic acids, and linear aliphatic diols such as butanediol and hexanediol.

High molecular weight polycaprolactone may be made by conventional methods for the polymerization of ε-caprolactone. Suitable polycaprolactones are commercially available, e.g. PCL-300 and PCL-700 of Union Carbide Corporation, also known by the brand names Tone P-300 and Tone P-700, respectively, having weight average molecular weights of about 15,000 and about 40,000, respectively, as reported by the manufacturer. Copolymers of caprolactone and another monomer may be made by conventional polymerization techniques, e.g. as described in U.S. Pat. No. 4,190,720.

When reference is made hereafter to polycaprolactone, this will include the above-described copolymers of caprolactone containing 10% or less of a biodegradable comonomer.

The high molecular weight polycaprolactone is applied to the multifilament suture generally from a solution in a solvent for polycaprolactone such as methylene chloride. Other known solvents for polycaprolactone may be used such as carbon tetrachloride, chloroform, ethyl acetate, cyclohexanone, methyl ethyl ketone, toluene, and xylene. The concentration of the polycaprolactone in the solvent may range from 1 to 10% by weight based on the solvent. Generally, about 5 g commercially available polycaprolactone per 100 ml of solvent is used. The preferred concentration will provide a readily flowable composition the solvent of which is not difficult to evaporate after the coating is applied, and will deposit the desired amount of polycaprolactone on the suture.

The sutures are immersed in the coating solution for 0.1 to 10 minutes, preferably about 0.2–3 minutes, and air dried at room temperature or, if desired, at slightly higher temperatures. The immersion may be carried out by batch dipping a skein or by continuously passing a continuous length of yarn through the coating solution.

The primary lubricating agent, high molecular weight polycaprolactone, may be mixed with other lubricating agents in an amount of up to 50% by weight of the combined lubricating agents. Examples of such other lubricating agents are poly(ethylene oxide), partially oxidized polyethylene wax, N,N'-ethylene diamine bis-stearamide, $C_{10}$–$C_{30}$ fatty acid esters of sterols such as cholesterol and lanosterol, and polyalkylene glycols such as a copolymer of ethylene glycol and propylene glycol.

The coating composition may also contain other components for other purposes including dyes, stabilizers against oxidation or degradation caused by radiation, antibiotics, antiseptics, analgesics, anesthetics, antiinflammatory agents, growth or healing promoting agents and other pharmaceutically active ingredients.

Polycaprolactone is known to be a non-toxic material that degrades slowly in living tissue to form an innocuous metabolizable intermediate.

The following examples illustrate the invention. Examples 1–15 and 20 are comparative examples and Examples 16–19 are examples according to the invention.

EXAMPLES 1–19

Uncoated sutures of polyglycolic acid (18 inch long) were immersed in 100 ml of coating solution. The solvent, percentage by weight of coating material in solution, percentage coating by weight on the coated suture, and the size of the sutures are listed in Table 1.

The sutures were immersed in the coating solution for 2 to 3 minutes and air dried at room temperature. The percentage coating was calculated by weighing the suture on an analytical balance before and after coating and is given in Table 1 as percent of total weight of the coated suture. After air drying, the coated sutures were stored in a desiccator.

TABLE 1

| Example | Suture size | Coating material | Solvent | % Coating material in solvent | % Coating on suture |
|---|---|---|---|---|---|
| 1 | 2-0 | PEO 8000 | $CH_2Cl_2$ | 3 | 1.4 |
| 2 | 2-0 | PGA powder | $CH_2Cl_2$ | 5 | 1.3 |
| 3 | 2-0 | PEO 8000-PGA powder (5:1) | $CH_2Cl_2$ | 3.5 | 1.5 |
| 4 | 2-0 | Plurocol P-4010 | $CHCl_3$ | 3 | 1.0 |
| 5 | 3-0 | PVP | $CHCl_3$ | 2 | 6.9 |
| 6 | 3-0 | PVP | $CHCl_3$ | 2 | 1.7 |
| 7 | 3-0 | PVA | $H_2O$ | 3 | 6.5 |
| 8 | 3-0 | PEO 8000-calcium stearate (2:1) | $CH_2Cl_2$ | 3 | 3.4 |
| 9 | 2-0 | Petrac 15 | $CHCl_3$ | 5 | 3.5 |
| 10 | 2-0 | Petrac 165 | $CHCl_3$ | 5 | 2.9 |
| 11 | 2-0 | PEG-100 stearate | $CH_2Cl_2$ | 5 | 4.4 |
| 12 | 2-0 | PEG-40 stearate | $CH_2Cl_2$ | 5 | 3.9 |
| 13 | 2-0 | Carnauba wax | $CHCl_3$ | 5 | 3.9 |
| 14 | 2-0 | Kemamide W-40 | $CHCl_3$ | 5 | 2.3 |
| 15 | 4-0 | Cholesteryl palmitate | $CHCl_3$ | 5 | 2.5 |
| 16 | 1-0 | PCL (Tone P300) | $CH_2Cl_2$ | 5 | 5.7 |
| 17 | 1-0 | PCL (Tone P700) | $CH_2Cl_2$ | 5 | 6.1 |
| 18 | 1-0 | PCL (Tone P700) Super Sterol Ester (1:1) | $CH_2Cl_2$ | 5 | 2.4 |
| 19 | 1-0 | PCL (Tone P700) Super Sterol Ester (4:1) | $CH_2Cl_2$ | 5 | 3.1 |

The abbreviations and trademarks in Table 1 stand for the following:
PEO: poly(ethylene oxide)
PGA: poly(glycolic acid)
Plurocol P-4010: poly(propylene glycol)
PVA: poly(vinyl pyrrolidone)
Petrac 165: wax
Petrac 215: partially oxidized polyethylene wax (Petrochemicals Company Inc.)
PEG: poly(ethylene glycol)
Kemamide: N,N′—ethylene diamine bis-stearamide
PCL: polycaprotone
Super Sterol Ester: cholesterol and lanosterol esters of a mixture of $C_{10}$—$C_{30}$ fatty acids esters, supplied by CRODA Inc.

The melt viscosity of PCL (Tone P300) was measured with a Brookfield RVT viscometer having a No. 7 spindle at 20 and 50 rpm. The polymer was melted in a beaker and surrounded by a temperature controlled water bath, the temperature of which was measured with an electronic thermometer sensitive to ±0.1° C. The viscosity was 51,200 cps at 60° C. PCL (Tone P700)) is solid at 60° C. The molecular weight of PCL (Tone P700) was determined by gel permeation chromatography and was found to be 100,000 (polystyrene equivalent in dichloromethane).

Table 2 sets out the properties of the coated sutures of Table 1.

The general texture and feel of a suture such as flexibility, smoothness and hardness was observed by handling the suture and drawing between fingers. Typical observations as set out in Table 2 are stiff, silky, waxy.

The slipdown property of a suture was determined by tieing tightly a two-throw square knot, then grasping the long ears and pulling apart. If the suture was drawn through the knot, giving the appearance of the knot slipping down the braid, it was marked as excellent (exc.), good, or acceptable (acc.) depending on the ease of slipdown. If the knot seized or was difficult to slip down, the suture was marked as locks, poor, or rachety, depending on the difficulty of slip down.

The slipdown property was also tested under wet conditions by immersion of the unknotted suture in water for 5 seconds and immediately testing thereafter.

The knot security of a suture was tested by tying firmly a triple throw square knot and pulling the suture from a patient's side until the knot slipped or the suture broke. If the knot slipped, knot security was marked poor. If the suture broke without slip, the knot was sufficient to hold the suture at the knot and was marked acceptable in Table 2.

The knot security was tested under wet conditions by immersion of the unknotted suture in water for 5 seconds and immediately testing thereafter.

The wet knot slipdown was tested by tieing tightly a two-throw granny knot and slipping down the knot. The knot was then wetted by rubbing with fingers dipped in water. An attempt was then made to slip the knot down further. If the knot slipped both dry and wet, the suture was marked as acceptable, good, or excellent depending on the ease of the slip. If the knot slipped dry but not wet, the suture was marked as locking. If the slip was poor wet and dry and locking was difficult to determine, the suture was marked poor, or rachety.

TABLE 2

| Example | Texture | 2 throw square slipdown dry | 2 throw square slipdown wet | 3 throw square slipdown dry | 3 throw square slipdown wet | 2 throw granny slipdown, wet knot | Comments |
|---|---|---|---|---|---|---|---|
| 1 | stiff | exc. | poor | acc. | acc. | locks | exc. dry, poor wet |
| 2 | powdery smooth | poor | locks | acc. | acc. | locks | poor lubr. overall |
| 3 | stiff | exc. | poor | acc. | acc. | locks | exc. dry, poor wet |
| 4 | silky | acc. | acc. | acc. | acc. | locks | acc. lubr. but locks |
| 5 | very stiff | poor | locks | acc. | acc. | locks | very poor lubr., locks |
| 6 | very stiff | locks | locks | acc. | acc. | locks | as 5 |
| 7 | stiff, rough | rachety | locks | acc | acc. | poor | poor lubr. esp. wet |
| 8 | silky | exc. | poor, rachety | acc. | acc. | locks | exc. slipdown dry, but not when wet |

TABLE 2-continued

| Example | Texture | 2 throw square slipdown dry | 2 throw square slipdown wet | 3 throw square slipdown dry | 3 throw square slipdown wet | 2 throw granny slipdown, wet knot | Comments |
|---|---|---|---|---|---|---|---|
| 9 | stiff, rough | exc. | exc. | acc. | acc. | exc., no locking | excellent |
| 10 | very rough | rachety | rachety | acc. | acc. | rachety | poor lubr., not affected by water |
| 11 | stiff, waxy | very good | good | acc. | acc. | rachety | fairly good, not much affected by water |
| 12 | stiff, smooth | rachety | rachety | acc. | acc. | rachety | poor lubr., not affected by water |
| 13 | rough | fine to rachety | good | acc. | acc. | acc. | rachety dry, good wet |
| 14 | waxy, rough | good | good | acc. | acc. | good | good, not affected by water |
| 15 | rough | poor | poor | acc. | acc. | poor | poor lubr. overall |
| 16 | stiff, waxy | exc. | exc. | acc. | acc. | exc. | as 14 |
| 17 | stiff, waxy | exc. | exc. | acc. | acc. | exc. | as 14 |
| 18 | silky, good feel | exc. | exc. | acc. | acc. | exc. | exc. good feel, good lubr., not affected by water |
| 19 | stiff | exc. | exc. | acc. | acc. | exc. | as 18. |

"lubr.": lubricant

COMPARATIVE EXAMPLE 20

An uncoated suture of polyglycolic acid (54 inch long), size 3-0 was immersed in 100 ml of coating solution comprising 95.0 ml methylene chloride and 5.00 g of Tone polyester 0240 (formerly Niax Polyol D560) of Union Carbide Corporation. The manufacturer specifies a molecular weight of 2000 and a viscosity of 500 cps at 60° C. for Tone polyester 0240. The coating solution was obtained by dissolving the Tone polyester 0240 at toom temperature in a 200 ml beaker in 3 minutes using a magnetic stirrer.

The suture was immersed in the coating solution for one minute and air-dried at room temperature. The % coating on the suture was 5.9.

Knot slip and knot security were determined as follows.

| Knot | Result |
|---|---|
| 2 throw square slip down | slips about 0.5 inch, locks and breaks |
| 3 throw square slipdown | locks |
| 2 throw granny slipdown (dry) | acceptable slip |
| 2 throw granny slipdown (wet) | acceptable slip |

I claim:

1. A surgical suture comprising a braided multifilament of poly(glycolic acid or a copolymer containing at least 85% glycolic acid units coated with a lubricating agent selected from the group consisting of a high molecular weight homopolymer of caprolactone, a high molecular weight copolymer of at least 90% by weight of caprolactone and the remainder another biodegradable monomer, and a blend of at least 50% by weight of said homopolymer of said copolymer of caprolactone and up to 50% by weight of another biodegradable lubricating agent, said homopolymer or copolymer of caprolactone having a melt viscosity at 60° C. of at least about 50,000 centipoise or being solid.

2. A suture according to claim 1 wherein said other biodegradable lubricating agent is a mixture of sterol esters of $C_{10}$–$C_{30}$ fatty acids.

3. A suture according to claim 2 wherein said sterol is a mixture of cholesterol and lanosterol.

4. A suture according to claim 1 wherein said lubricating agent is present in an amount of 0.5 to 10% by weight based on the weight of the suture.

5. A needled surgical suture comprising at least one filament of poly(glycolic acid) or a copolymer containing at least 85% glycolic acid units coated with a lubricating agent selected from the group consisting of a high molecular weight homopolymer of caprolactone, a high molecular weight copolymer of at least 90% by weight of caprolactone and the remainder another biodegradable monomer, and a blend of at least 50% by weight of said homopolymer or said copolymer of caprolactone and up to 50% by weight of another biodegradable lubricating agent, said homopolymer or copolymer of caprolactone having a melt viscosity of 60° C. of at least about 50,000 centipoise.

6. A needled surgical suture according to claim 5 wherein said other biodegradable lubricating agent is a mixture of sterol esters of $C_{10}$–$C_{30}$ fatty acids.

7. A surgical suture package comprising a sterile enclosure containing a sterile needled surgical suture, the suture comprising at least one filament of poly(glycolicacid) or a copolymer containing at least 85% glycolic acid units coated with a lubricating agent selected from the group consisting of a high molecular weight homopolymer of caprolactone, a high molecular weight copolymer of at least 90% by weight of caprolactone and the remainder another biodegradable monomer, and a blend of at least 50% by weight of said homopolymer of said copolymer of caprolactone and up to 50% by weight of another biodegradable lubricating agent, said homopolymer or copolymer of caprolactone having a melt viscosity at 60° C. of at least about 50,000 centipoise or being solid.

8. A package according to claim 7 wherein said other biodegradable lubricating agent is a mixture of sterol esters of $C_{10}$–$C_{30}$ fatty acids.

* * * * *